US011135107B2

(12) United States Patent
Espinosa De Los Monteros et al.

(10) Patent No.: US 11,135,107 B2
(45) Date of Patent: Oct. 5, 2021

(54) ABSORBENT, DISPOSABLE, RE-FASTENABLE UNDERGARMENT

(71) Applicant: Grupo P.I. Mabe, S.A. De C.V., Puebla (MX)

(72) Inventors: Carlos Canales Espinosa De Los Monteros, Puebla (MX); Lucía del Carmen Sanchez Fernandez, Puebla (MX)

(73) Assignee: GRUPO P.I. MABE, S.A. DE C.V., Puebla (MX)

( * ) Notice: Subject to any disclaimer, the term of this patent is extended or adjusted under 35 U.S.C. 154(b) by 768 days.

(21) Appl. No.: 15/537,825

(22) PCT Filed: Nov. 24, 2015

(86) PCT No.: PCT/IB2015/059104
§ 371 (c)(1),
(2) Date: Jun. 19, 2017

(87) PCT Pub. No.: WO2016/097906
PCT Pub. Date: Jun. 23, 2016

(65) Prior Publication Data
US 2018/0036183 A1    Feb. 8, 2018

(30) Foreign Application Priority Data
Dec. 19, 2014    (MX) .................... MX/a/2014/016122

(51) Int. Cl.
*A61F 13/56*    (2006.01)
*A61F 13/49*    (2006.01)
(Continued)

(52) U.S. Cl.
CPC .... *A61F 13/5655* (2013.01); *A61F 13/15203* (2013.01); *A61F 13/496* (2013.01);
(Continued)

(58) Field of Classification Search
CPC combination set(s) only.
See application file for complete search history.

(56) References Cited

U.S. PATENT DOCUMENTS

| 5,899,896 A | * | 5/1999 | Suprise | ................. A61F 13/622 604/391 |
|---|---|---|---|---|
| 6,447,497 B1 | | 9/2002 | Olson | |

(Continued)

FOREIGN PATENT DOCUMENTS

| EP | 1559386 A2 | 8/2005 | | |
|---|---|---|---|---|
| EP | 2 359 789 | * | 8/2011 | ........... A61F 13/505 |

(Continued)

OTHER PUBLICATIONS

International Search Report for PCT/IB2015/059104 dated Mar. 10, 2016, 8 pages.

*Primary Examiner* — Michele M Kidwell
(74) *Attorney, Agent, or Firm* — VIVICAR Law, PLLC

(57) ABSTRACT

The present invention protects a refastenable disposable absorbent pant, comprised by a chassis, left and right front side panels, and left and right rear side panels, in such a way that the left and right front side panels are joined to the left and right rear side panels, respectively, by means of a refastenable seal, such that the pant has an arrangement suitable to be pulled up and down through the legs, with a waist opening and a pair of leg openings, such that the left and right front panels are wider than the left and right rear panels, and the refastenable seal is placed at the rear part of the pant, between the side flanks thereof and the longitudinal edges of the chassis.

12 Claims, 3 Drawing Sheets

(51) Int. Cl.
*A61F 13/15* (2006.01)
*A61F 13/496* (2006.01)
*A61F 13/53* (2006.01)
*A61F 13/62* (2006.01)

(52) U.S. Cl.
CPC .. *A61F 13/49011* (2013.01); *A61F 13/49014* (2013.01); *A61F 13/49015* (2013.01); *A61F 13/49017* (2013.01); *A61F 13/53* (2013.01); *A61F 13/5633* (2013.01); *A61F 13/622* (2013.01); *A61F 2013/49084* (2013.01); *A61F 2013/49088* (2013.01); *A61F 2013/530131* (2013.01)

(56) References Cited

U.S. PATENT DOCUMENTS

| | | | |
|---|---|---|---|
| 6,447,628 B1 | 9/2002 | Couillard et al. | |
| 6,454,475 B2 | 9/2002 | Giles et al. | |
| 6,645,190 B1 | 11/2003 | Olson et al. | |
| 6,761,711 B1 | 7/2004 | Fletcher et al. | |
| 6,849,067 B2 | 2/2005 | Fletcher et al. | |
| 6,893,426 B1 | 5/2005 | Popp et al. | |
| 7,695,464 B2 | 4/2010 | Fletcher et al. | |
| 7,833,207 B2 | 11/2010 | Kenmochi et al. | |
| 8,052,666 B2 | 11/2011 | Sawyer et al. | |
| 8,123,733 B2 | 2/2012 | O'Connell | |
| 8,287,512 B2 | 10/2012 | Gabriele | |
| 8,551,065 B2 | 10/2013 | Angelis | |
| 8,579,876 B2 | 11/2013 | Popp et al. | |
| 8,747,379 B2 | 6/2014 | Fletcher et al. | |
| 2002/0111596 A1* | 8/2002 | Fletcher | A61F 13/565 604/385.03 |
| 2004/0034327 A1 | 2/2004 | Kuen et al. | |
| 2005/0027271 A1* | 2/2005 | Popp | A61F 13/5511 604/385.01 |
| 2007/0016155 A1* | 1/2007 | Chang | A61F 13/49011 604/385.3 |
| 2013/0231627 A1 | 9/2013 | O'Connell | |

FOREIGN PATENT DOCUMENTS

| | | | | |
|---|---|---|---|---|
| GB | 2283660 A | | 5/1995 | |
| MX | 623 | | 7/1993 | |
| MX | 2008016404 A | | 2/2009 | |
| WO | 99/60966 | * | 12/1999 | ............ A61F 13/15 |
| WO | 2006039242 A2 | | 4/2006 | |
| WO | 2007/123445 | * | 11/2007 | ........... A61F 13/496 |
| WO | 2013/132368 | * | 9/2013 | ............ A61F 13/56 |

* cited by examiner

ABSORBENT, DISPOSABLE, RE-FASTENABLE UNDERGARMENT

CROSS-REFERENCE TO RELATED APPLICATIONS

This is a national stage patent application of PCT/IB2015/059104, filed on Nov. 24, 2015 entitled "ABSORBENT, DISPOSABLE, RE-FASTENABLE UNDERGARMENT," and claims priority from Mexican Patent Application No. MX/a/2014/016122, filed Dec. 19, 2014, both of which are incorporated by reference in their entirety.

BACKGROUNDS OF THE INVENTION

A disposable absorbent pant is a disposable absorbent article that may be pulled up and down through the legs, such as a disposable absorbent pant as usually used as underwear. There are in the market several kind of disposable absorbent pants with different designs depending on their use: for babies, for toddlers, for youngsters and for adults. There are also disposable absorbent pants with such an arrangement that they may be used as pants or as diapers.

An example of an arrangement of a disposable absorbent pant for toddlers or babies that is known in the art is the one that consists of a main body or chassis and side panels at the front and rear parts thereof; the front and rear panels are joined together to form the disposable absorbent pant with a waist opening and a pair of leg openings. The side panels, preferably, are elastic. In other arrangements, the panels are integral parts of the chassis and are formed by enlarging the layers that form same.

A very appreciated characteristic in a disposable absorbent pant is that same is refastenable, i.e., that it may be opened and closed again in order to verify if the article has already been used or in order to readjust the article to the body of the user. There are a number of proposals aimed to refastenable disposable absorbent pants, e.g., Mexican Utility Model No. 623 owned by the present applicant and with priority date of Jul. 21, 1993, describes a disposable absorbent pant with side seals that may be opened and closed again, thereafter many proposals of refastenable disposable pants have been made, most of which describe the use of refastenable fastening elements provided between two panels that are permanently joined to the chassis by the front and rear parts thereof, and that are joined by the side parts of the pants, this is the case of U.S. Pat. Nos. 6,849,067, 8,579,876, 6,645,190, 8,747,379, 6,454,475, 6,447,628, 6,447,497, 8,052,666, 6,893,426, 7,695,464 and 6,761,711, all of them assigned to Kimberly Clark and which protect different arrangements of front and rear panels, as well as fastening elements and methods of placement thereof; other patents that also refer to disposable absorbent pants with front and rear panels with different arrangements and with refastenable seals are cited as follows: U.S. Pat. No. 7,833,207 of Uni Charm Corporation, U.S. Pat. Nos. 8,551,065 and 8,287,512 of Fameccanica, patent U.S. Pat. No. 8,123,733 of First Quality Baby Products.

In all these proposals, the pant has a refastenable seal placed in each of the side parts of the pant; these refastenable seals are generally formed joining two mechanical matching fastening elements, such as hooks and loops, system that is known in the market as Velcro®; the element with the hooks is placed at the edges of the rear panels and the element with the loops is placed at the front panels in such a way that when same are attached they form the pant-like diaper, with a waist opening, two leg openings and with the refastenable seals at the side parts thereof, being extended from the waist opening to the leg opening of the pant. This kind of mechanical fastening system has the drawback that it lacks of the flexibility and softness required for the user of the pant to not notice same and to feel totally comfortable. When these seals are placed at the side parts of the pant, such as in the designs proposed in the cited patents, the stress caused by the movements of the user may misalign the seal or even open it, on the other hand, there is the risk that the user, when moving or bending, may be injured by same.

Patent application US20130231627 of First Quality Baby Products describes a disposable absorbent pant with refastenable front and rear side panels provided at the front part of the pant, in such a way that the rear panels are wider than the front panels and both are joined with a Velcro®-type mechanical seal through the front part of the pant. The seal described in the cited patent application is even more uncomfortable for the user, as it is placed by the front part of the pant, at the sides of the abdomen, and with the normal movements of the user, when seating or bending, this part of the body is bended forward and the seals may make the user feel uncomfortable.

The design of the refastenable absorbent pant of the present invention solves this problem with a design in which the refastenable seal of the pant is provided at the rear part thereof, in the buttock of the user, a part of the body that is not bended with the movements of the user such that the refastenable seals, when being provided in a part of the body that may not be bended, do not make the user feel uncomfortable nor may injure same, on the other hand, in the area in which the seal is placed there are no strengths which could misalign same.

The refastenable absorbent pant of the present invention has the following arrangement:
- a chassis, comprised by a permeable top layer, a watertight bottom layer and an absorbent core provided between both top and bottom layers. The chassis has a front part, a rear part and a crotch part, two longitudinal edges and two transversal edges.
- a pair of front side panels and a pair of rear side panels, such that the front side panels are wider than the rear side panels.
- a refastenable fastening system for joining the left front side panel with the left rear side panel, and the right front side panel with the left front side panel.

SUMMARY OF THE INVENTION

The object of the present invention is to provide a disposable absorbent pant arrangement with front and rear side panels and with a refastenable seal therebetween that is comfortable and safe for the user.

Other object of the invention is that the refastenable seals are placed in the rear part of the disposable absorbent pant.

An additional object of the invention is that the refastenable seal is not bended or opened during the use of the article.

Other object of the invention is that the refastenable seal may not be reached by the user.

DETAILED DESCRIPTION OF THE INVENTION

A disposable absorbent pant is an article that is designed so that it may be pulled up and down through the legs, i.e., it has the shape of a common pant with a waist opening and an opening for each of the legs. Some disposable absorbent pants are refastenable, in such a way that the caregiver may open the article in order to readjust same or to verify the state of use thereof, and it has the possibility of closing it again without damaging it or undermining its functionality.

The present invention protects an absorbent pant with front and rear side panels refastenably joined together, such that the front panels are wider than the rear panels and the refastenable seals are placed between the side flanks of the pant and the longitudinal rear edges of the chassis, such that they do not make the user feel uncomfortable with the normal movements thereof as they are never drastically bended as it could happen if same were placed at the side parts or at the front part of the pant. On the other hand, its functionality is not affected by the strengths exerted by the natural movements of the user.

Figure 1:
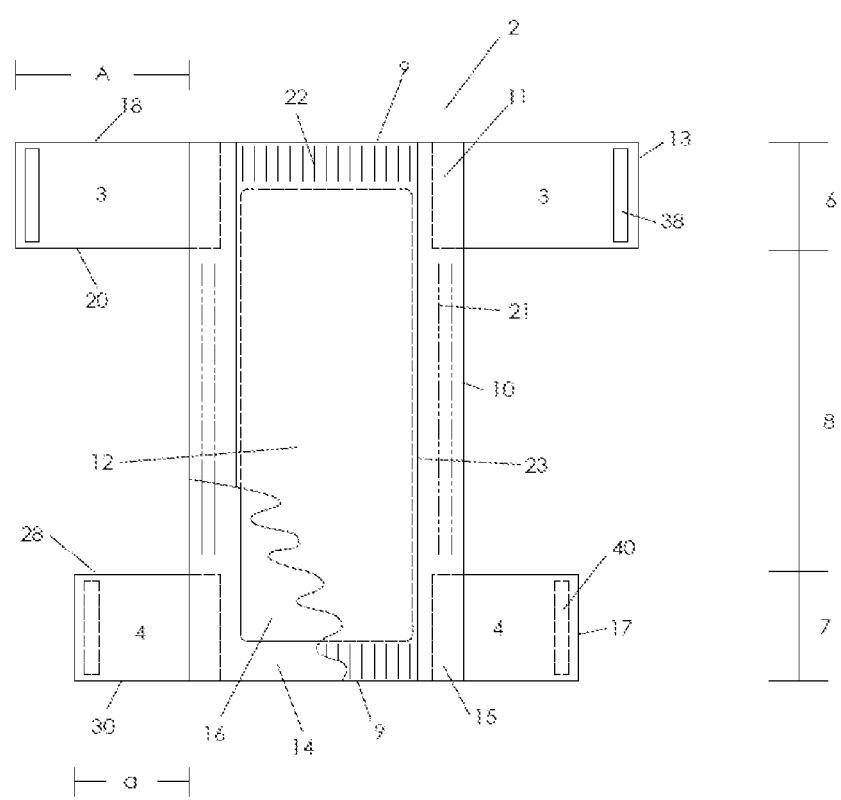
FIG. 1 shows the inner part of the disposable absorbent pant of the invention before being transversally bended and attached by means of the front and rear side panels.

The absorbent pant of the present invention is comprised, as may be seen in FIG. 1, by a chassis (2), a pair of front side panels (3) and a pair of rear side panels (4).

The chassis (2) is comprised by an inner layer (12), an outer layer (14) and an absorbent core (16) placed therebetween; it has a front part (6), a rear part (7) and a crotch part (8) between the front (6) and rear (7) parts, two transversal edges (9) and two longitudinal edges (10); the longitudinal edges have a front part, a rear part and a crotch part matching the front, rear and crotch parts of the chassis, which may further have elastic crotch areas (21) adjacent to the longitudinal edges through the crotch area (8), elastic waist areas (22) adjacent to the transversal edges through the front (6) and rear (7) part of the chassis (2). Anti-leakage barriers (23) and one or more transfer layers (not shown in the drawings).

The inner layer (12) is the one that will be in contact with the skin of the user, so it must be soft, flexible and allow for the pass of fluids. An hydrophilic non-woven fabric or with hydrophilic areas with a base weight between 7 and 40 g/m$^2$ is generally used as the inner layer (12). This non-woven fabric may be comprised by synthetic and/or natural fibers, single or multi-components, it may be flat, embossed or perforated and may be made by any known method (spundbond, meltblown, teased, spunmelt, airlay, fibrillation, etc.) or combinations thereof.

The outer layer (14) is the one that faces outside the article and its main function is to stop the exudates and to avoid the clothing in contact with the article to get dirty, so it must be watertight; moreover, it is the layer that gives the outer appearance to the article; preferably, a non-woven fabric laminated with a polymeric film is used, such that the non-woven fabric is the part of the laminated material that is placed facing outwards and the polymeric film facing inwards, thus achieving the required watertightness and a fabric-like appearance very appreciated in this kind of articles. The polymeric film and/or the non-woven fabric may be printed or have any specific color, such that the disposable absorbent pant may resemble as much as possible the underwear.

The absorbent core (16) is the part of the article in charge of absorbing and retaining the exudates that pass through the inner layer (12), it may be comprised by fibers of absorbent material mixed with particles or fibers of super absorbent material in the desired ratio, from 100:0 to 0:100.

The elastic crotch areas (21) are achieved by joining in a tensed manner an elastomeric material at the crotch part of the chassis (10) thereof. The elastomeric material may be comprised by threads or elastic bands, elastomeric laminated material or any other material known in the art that is capable of the required stretching and retraction. It may be joined between the inner (12) and outer layers (14), over the inner layer (12) or over the outer layer (14) of the chassis.

The elastic waist areas (22) are comprised by an elastic or elastomeric material joined to the chassis (2) by the front part (6), by the rear part (7) or by both parts, the front (6) and the rear (7) adjacent to the transversal edges (9) of the chassis. The elastic or elastomeric material may be joined between the inner (12) and outer (14) layers, over the inner layer (12) or over the outer layer (14).

The anti-runoff barriers (23) are a pair of barriers placed adjacent to the longitudinal edges (10) of the chassis (2), over the inner layer (12) thereof. The barriers have a proximal edge joined to the inner layer (12) and an edge distal from the inner layer (12) so as to form the barrier. There are a number of arrangements for anti-leakage barriers known in the art, all of which may be used in the article protected by this invention.

The transfer layer is a layer that is generally placed between the permeable top layer and the absorbent core and which contributes to the good distribution of fluids within the core, and to reduce the amount of fluid that returns to the top layer surface, so that the article works more efficiently. Generally, a non-woven fabric with the suitable characteristics of weigh, composition, strengths, etc., is used to achieve the described objects.

Further, the disposable absorbent article of the present invention may include some kind of wetness indicator or sensor that helps the caregiver determine when to change the pant. The front (3) and rear (4) side panels of the disposable absorbent pant of the invention are made of a soft and flexible material that adjusts into the body of the user without injuring him; they may be elastic, non-elastic or they may have elastic and non-elastic areas. The panels have an inner face (24) facing the user and an outer face (26) facing outside the user.

In the case of non-elastic panels, a non-woven fabric with the softness, base weight and strengths required to avoid scratching and deformation of the panel during the use may be used to form the panel. A non-woven fabric suitable for this purpose has the following characteristics: 20 to 100 g/m$^2$ base weight; 300 g/cm minimum longitudinal strength; 200 g/cm minimum transversal strength.

In the case of elastic panels, an elastic laminated material comprised by at least two layers, one elastic such as threads, bands, foams or elastic films, and another one non-elastic that is generally a non-woven fabric, may be used; a 3 layers elastic laminated material is preferably used, two non-woven fabric layers and one elastic layer therebetween. The layers may be joined by any means known, such as adhesive, ultrasonic, heat, etc. Also a single layer of an elastic non-woven fabric may be used.

Materials with this characteristics are known in the field to achieve a good adjustment of the pant to the body of the user and so that the pant may be pulled up and down through the legs several times, the material of the side panels must have certain elongation and certain retraction strength. A suitable material for this purpose shall elongate 50% using a strength within 50 and 100 g/cm and 100% using a strength within 100 and 150 g/cm. On the other hand, the elastomeric materials have certain reduction in the stress strength during its use, i.e., the stress strength required to elongate them reduces once they are stretched for the first time; an elastomeric material suitable to be used in the disposable absorbent article of the present invention shall have a maximum 50% reduction in the stress strength after stressing certain predetermined strength during 60 seconds. The reduction in the stress strength is measured according to the following method.

1. A strip of the material to be measured is cut at 75 mm width and a length enough to be placed in a dynamometer with a gap between jaws of 2.54 cm.
2. The strip is held between the clamps of the dynamometer and a stretch strength F1 of 1 kg of force is applied thereto.
3. The opening between the clamps of the dynamometer is maintained during 60 seconds.
4. The stretching strength is measured at 60 seconds (F2).
5. The % of reduction of stretching strength is calculated as:

stretching strength reduction %=(1−$F2/f1$)*100

In one embodiment of the invention, the panels may be mixed, i.e., with one or more non-elastic areas and one or more elastic areas, in this case, the panels may be formed by joining elastic and non-elastic materials such as those described above, or may be comprised by elastic materials with dead or non-elastic areas.

The left and right front panels (3) of the disposable absorbent pant of the present invention have a proximal edge (11) that is the one that joins to each of the front parts of the longitudinal edges of the chassis (2), and a distal edge (13) that is the one which refastenably joins to the rear panels (4), as well as a top edge (18) and a bottom edge (20).

The left and right rear panels (4) of the disposable absorbent pant of the present invention have a proximal edge (15) that is the one that joins to each of the rear parts of the longitudinal edges of the chassis (2), and a distal edge (17) that is the one that refastenably joins to the front panels (3); likewise, they have a top edge (28) and a bottom edge (30).

Figure 2:
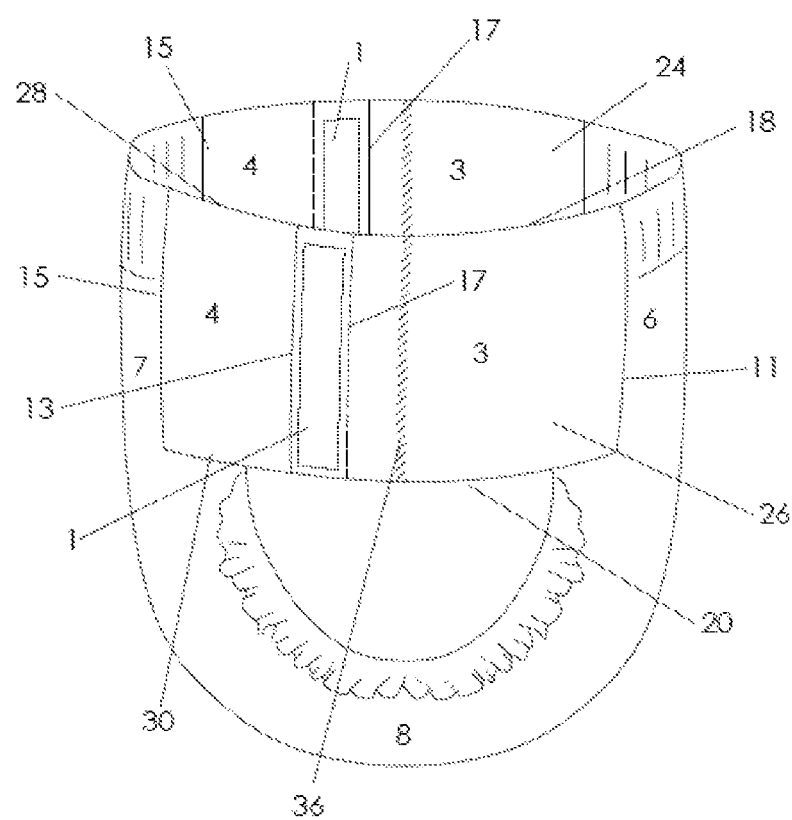
FIG. 2 shows a side view of the disposable absorbent pant of the invention in an arrangement suitable for its use.

FIG. 2 shows the absorbent pant of the invention in an arrangement suitable for its use, with the front (3) and rear (4) front side panels joined by the refastenable seal (1), such that the pant has a suitable arrangement for its use with a waist opening and two leg openings, as well as two side flanks (36) which are the parts of the disposable absorbent pant that are placed by the side hip parts of the user during use and have been marked in FIG. 2, solely for illustration purposes, as a small shadow.

As shown in FIGS. 1 and 2, in the disposable absorbent pant of the invention, the front panels (3) are wider than the rear panels (4) such that, when joining both front and rear panels through the refastenable seal (1), this is placed at the rear part of the pant between the side flanks (36) of the pant and the rear part of the longitudinal edges of the chassis (2); in this way, when the user seats, bends or makes any movement, the refastenable seal (1) does not hurt him nor makes him feel uncomfortable as it is practically impossible for the user to bend backwards by the waist, on the other hand, the seal (1) works more efficiently as it is not subjected to stresses and bending caused by the movements of the user. The placement of the refastenable seal at the rear part further has the advantage that, if the user is a baby or a toddler, he has no access to the seal so it is difficult for him to open same by himself, situation that is feasible when the seal is placed at the side parts or at the front part of the pant. Likewise, the detachment thereof is prevented, which could be caused by the friction with buttons, zippers, pins, etc.

Thus, for the objects of the present invention, the front panels have a width "A" and the rear panels have a width "a", such that A/a>1.

On the other hand, in order to prevent the refastenable seal (1) from opening during use, it is required that same has a minimum 1500 g shear strength, considering the whole panel, as well as a minimum 300 g peel strength, considering the whole panel. The shear strength is achieved by pulling each of the panels in an opposed direction, while the peel strength is achieved by opening the seal and pulling one of the panels at 90°.

Each of the front (3) and rear (4) panels of the pant of the invention has a top edge (18 and 28) and a bottom edge (20 and 30). For both the front panels (3) and for the rear panels (4), the top edge (18 and 28) is generally straight and is aligned with the transversal edge (9) of the chassis (2), although it may have any other shape and be slightly above or slightly below the transversal edge (9) of the chassis (2).

Regarding the bottom edge (20 and 30) of the panels, it may be a straight line parallel to the top edge thereof, as shown in FIG. 1, or it may have several shapes that contribute to a better adjustment and to the comfort of the user provided that, for the front panels (3), the length of the proximal edge (11) is ≤the length of the distal edge (13), and for the rear panels (4), the length of the proximal edge (15) is ≥the length of the distal edge (17).

Figure 3:
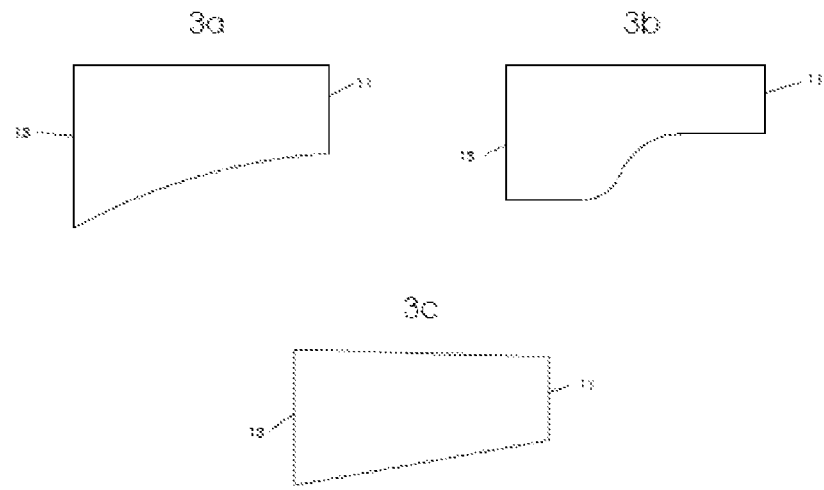
FIGS. 3A, 3B and 3C show different alternatives of the shape of the front panels of the disposable absorbent pant of the invention.
Figure 4:
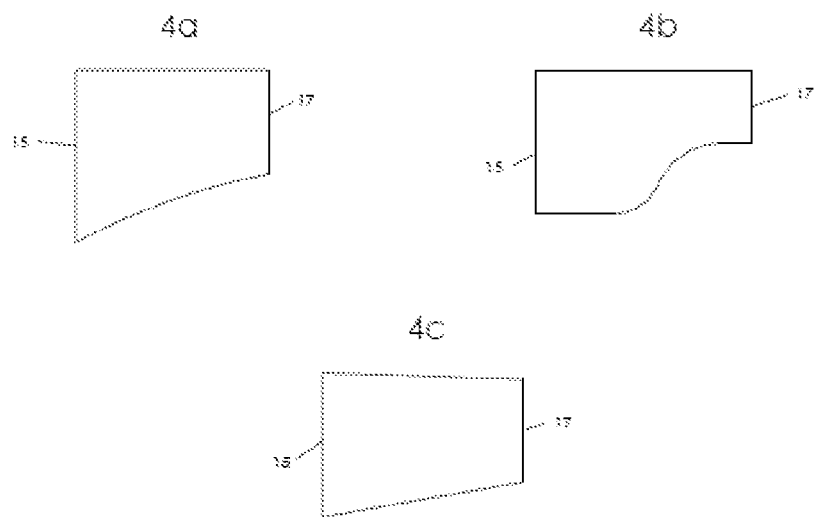
FIGS. 4A, 4B and 4C show alternatives of the rear panels of the disposable absorbent pant of the present invention.

Examples of some shapes for the front panels (3) are illustrated in FIGS. 3A, 3B and 3C and for the rear panels (4) in FIGS. 4A, 4B and 4C.

The front (3) and rear panels (4) are joined to the longitudinal edges of the chassis by the front and rear parts thereof through its proximal edge (11 and 15) by means of adhesive, thermal bonding, ultrasonic bonding or any other means known or combination thereof, such that they are not detached from the chassis during use.

The refastenable seal (1) that attaches each of the left and right front panels (3) with the corresponding rear panel (4), preferably is a mechanical seal, such that a first mechanical fastening element (38) is provided adjacent to the distal edge (13) of each of the front panels (3), by the inner face (24) thereof, and a second mechanical fastening element (38) is provided adjacent to each of the distal edges (17) of the rear panels (4) by the outer face (26) thereof. So the attachment between the mechanical fastening (38 and 40) define the refastenable seal (1). In an alternative of the invention, the first mechanical fastening element (38) is provided adjacent to the distal edge (13) of each of the front panels (3) by the outer face (26) thereof, and a second mechanical fastening element (40), that couples to the first element (38), is provided adjacent to each of the distal edges (17) of the rear panels (4) by the inner face (24) thereof.

Preferably, a hook & loop type system is used as the fastening system, known in the market as Velcro®-type fastening system; the first fastening element (38) may interchangeably be the part of the system that contains the hooks or the part of the system that contains the loops and the second fastening element (40) may interchangeably be the part of the system that contains the hooks or the part of the system that contains the loops.

The first (38) and second (40) fastening elements may have any arrangement suitable for this purpose, may be rectangular, be comprised by straight or curved parallel lines or any other desired arrangement. In another alternative of the method, not shown, anyone of the fastening elements (first (38) or second (40)) is the same material of the front (3) or rear (4) panel, which may be refastenably joined to the opposite panel which has the complementary fastening element attached thereto by the inner (24) or outer (29) face.

While the invention has been described according to the preferred embodiments, it is clear that several changes and modifications may be made thereto, such changes and modifications are within the spirit and scope of the invention as defined by the appended claims.

The invention claimed is:

1. A refastenable disposable absorbent pant comprised by a chassis, left and right front side panels and left and right rear side panels, such that the front side panels are joined to the rear side panels, respectively, by means of a refastenable seal, such that the pant has an arrangement suitable to be pulled up and down through the legs, with a waist opening, a pair of leg openings and two side flanks, wherein:

the chassis has a front part, a rear part and a crotch part between the front and rear parts, two transversal edges and two longitudinal edges, and the left and right front and left and right rear side panels each have an inner face facing the user during use, an outer face, a proximal edge permanently attached to the chassis, a distal edge, a top edge and a bottom edge, wherein the left and right front side panels are wider than the left and right rear side panels, such that the refastenable seal is formed by joining, in a refastenable manner, the distal edges of each of the front and rear side panels, so that the seal is placed at the rear part of the pant, between the side flanks and the longitudinal edges of the chassis, wherein the length of the distal edge of the front side panels is greater than the length of the proximal edge of the front side panels, and wherein the length of the distal edge of the rear side panels is smaller than the length of the proximal edge of the rear side panels.

2. The disposable absorbent pant as claimed in claim 1, wherein the front and rear side panels are formed from a material with elastic properties.

3. The disposable absorbent pant as claimed in claim 2, wherein the material of the front and rear side panels may be stretched 50% applying a strength between 60 and 100 g/cm.

4. The disposable absorbent pant as claimed in claim 2, wherein the material of the front and rear side panels is an elastic nonwoven web, a laminated material comprised by three layers: two layers of non-woven fabric and one layer of stretchable polymeric film therebetween or a laminated material comprised by three layers: two layers of non-woven fabric and one layer of elastic threads placed in parallel among them therebetween.

5. The disposable absorbent pant as claimed in claim 1, wherein the left and right side panels have elastic parts and non-elastic parts.

6. The disposable absorbent pant as claimed in claim 1, wherein the proximal edge of the front and rear side panels is permanently attached to the chassis by means of adhesive, using pressure and heat, by means of ultrasound or a combination thereof.

7. The disposable absorbent pant as claimed in claim 1, wherein the refastenable seal is comprised by a first mechanical fastening element and a second mechanical fastening element that couples to the first element.

8. The disposable absorbent pant as claimed in claim 7, wherein the refastenable seal is a hook & loop system.

9. The disposable absorbent pant as claimed in claim 7, wherein the first fastening element is placed over the inner face of each of the front panels, adjacent to the distal edge thereof and the second fastening element is placed over the outer face of each of the rear panels, adjacent to the distal edge thereof.

10. The disposable absorbent pant as claimed in claim 7, wherein the first fastening element is placed over the outer face of each of the front panels, adjacent to the distal edge thereof and the second fastening element is placed over the inner face of each of the rear panels, adjacent to the distal edge thereof.

11. The disposable absorbent pant as claimed in claim 7, wherein the first fastening element is placed over the inner face of each of the front panels and the second fastening element is comprised by the outer face of each of the rear panels.

12. The disposable absorbent pant as claimed in claim 7, wherein the first fastening element is placed over the inner face of each of the rear panels and the second fastening element is comprised by the outer face of the front panels.

* * * * *